(12) United States Patent
Lee et al.

(10) Patent No.: US 11,867,675 B2
(45) Date of Patent: Jan. 9, 2024

(54) NANOCOMPOSITE COMPRISING TWO-DIMENSIONAL NANO THIN FILMS FORMED ON AU NANOPARTICLE SURFACE AND METHOD FOR MANUFACTURING SAME

(71) Applicant: INDUSTRY-ACADEMIC COOPERATION FOUNDATION, YONSEI UNIVERSITY, Seoul (KR)

(72) Inventors: Kyu Hyoung Lee, Seoul (KR); Changhyun Jin, Incheon (KR); Myung Sik Choi, Yangju-si (KR)

(*) Notice: Subject to any disclaimer, the term of this patent is extended or adjusted under 35 U.S.C. 154(b) by 342 days.

(21) Appl. No.: 17/378,338

(22) Filed: Jul. 16, 2021

(65) Prior Publication Data

US 2022/0018019 A1    Jan. 20, 2022

(30) Foreign Application Priority Data

Jul. 17, 2020  (KR) ........................ 10-2020-0088600

(51) Int. Cl.
| | | |
|---|---|---|
| *G01N 33/00* | (2006.01) | |
| *C23C 16/18* | (2006.01) | |
| *C23C 16/46* | (2006.01) | |
| *G01N 27/12* | (2006.01) | |

(52) U.S. Cl.
CPC ......... *G01N 33/0027* (2013.01); *C23C 16/18* (2013.01); *C23C 16/46* (2013.01); *G01N 27/125* (2013.01); *G01N 27/127* (2013.01)

(58) Field of Classification Search
CPC ........ C23C 16/18; C23C 16/46; G01N 27/04; G01N 27/12; G01N 27/128; G01N 27/125; G01N 27/127; G01N 33/0004; G01N 33/0009; G01N 33/0027
See application file for complete search history.

(56) References Cited

U.S. PATENT DOCUMENTS

| | | | |
|---|---|---|---|
| 2006/0196248 A1* | 9/2006 | Nakano | G01N 27/125 73/31.06 |
| 2010/0072065 A1* | 3/2010 | Naito | G01N 27/12 204/424 |
| 2019/0369040 A1* | 12/2019 | Drmosh | G01N 33/0037 |

OTHER PUBLICATIONS

Mohammad Jafar Molaei, "The optical properties and solar energy conversion applications of carbon quantum dots," Solar Energy 196 (2020) 549-566.
Thi Ha Tran et al., "Facile fabrication of sensitive surface enhanced Raman scattering substrate based on CuO/Ag core/shell nanowires," Applied Surface Science 509 (2020) 145325.
(Continued)

*Primary Examiner* — Benjamin R Schmitt
(74) *Attorney, Agent, or Firm* — ANTONIO HA & U.S. Patent, LLC

(57) ABSTRACT

According to embodiments of the disclosure, a gold (Au)-embedded triple-layer $SnO_2$ nanocomposite comprises three layers of $SnO_2$—Au—$SnO_2$-x ($0<x<2$), wherein the Au is buried between the $SnO_2$ and $SnO_{2-x}$ ($0<x<2$) layers. Also provided is a method for manufacturing the AU-embedded $SnO_2$ nanocomposite.

11 Claims, 11 Drawing Sheets

(56) References Cited

OTHER PUBLICATIONS

Rusoma Akilimali et al., "Graphene nanoribbon-TiO2-quantum dots hybrid photoanode to boost the performance of photoelectrochemical for hydrogen generation," Catalysis Today 340 (2020) 161?169.

Prateek Sharma et al., "Colloidal MoS2 quantum dots based optical sensor for detection of 2,4,6-TNP explosive in an aqueous medium," Optical Materials 100 (2020) 109646.

Dhanasekaran Vikraman et al., "Direct synthesis of thickness-tunable MoS2 quantum dot thin layers:Optical, structural and electrical properties and their application to hydrogen evolution," Nano Energy 35 (2017) 101-114.

Shuang Cao et al., "Photocatalytic pure water splitting with high efficiency and value by Pt/porous brookite TiO2 nanoflutes," Nano Energy 67 (2020) 104287.

Hui Li et al., "Novel Construction of Morphology-Tunable C?N/SnO2/ZnO/Au Microspheres with Ultrasensitivity and High Selectivity for Triethylamine under Various Temperature Detections," ACS Appl. Mater. Interfaces 2019, 11, 8601?8611.

Chavi Mahala et al., "Near-Field and Far-Field Plasmonic Effects of Gold Nanoparticles Decorated on ZnO Nanosheets for Enhanced Solar Water Splitting," ACS Appl. Nano Mater. 2020, 3, 1153?1165.

Olivier Ouellette et al., "Spatial Collection in Colloidal Quantum Dot Solar Cells," Adv. Funct. Mater. 2020, 30, 1908200.

Jaemin Kim et al., "Ultrathin Quantum Dot Display Integrated with Wearable Electronics," Adv. Mater. 2017, 29, 1700217.

Huimei Duan et al., "Pentacoordinated Al3+-Stabilized Active Pd Structures on Al2O3-Coated Palladium Catalysts for Methane Combustion," Angew. Chem. Int. Ed. 2019, 58, 12043 ?12048.

Tanmoy Das, "Tuning directional dependent metal?insulator transitions in quasi-ID quantum wires with spin?orbit density wave instability," J. Phys.: Condens. Matter 28 (2016) 294001 (5pp).

Benjamin L. Greenberg et al., "Metal-insulator transition in a semiconductor nanocrystal network," Greenberg et al., Sci. Adv. 2019;5:caaw1462.

David J. Norris, "Multispectral quantum-dot photodetectors," Nature Photonics | vol. 13 | Apr. 2019 | 225?232.

Xiongjian Huang et al., "Reversible 3D laser printing of perovskite quantum dots inside a transparent medium," Nature Photonics | vol. 14 | 82 Feb. 2020 | 82?88.

Mina Zare et al., "Novel Green Biomimetic Approach for Synthesis of ZnO-Ag Nanocomposite; Antimicrobial Activity against Foodborne Pathogen, Biocompatibility and Solar Photocatalysis," Scientific Reports | (2019) 9:8303.

Jae Hoon Bang, "New type of doping effect via metallization of surface reduction in SnO2," Scientific Reports (2019) 9:8129.

Huiting Lu et al., "Graphene Quantum Dots for Optical Bioimaging," Small 2019, 15, 1902136.

Synthesis of Au/SnO2 nanostructures allowing process variable control, Myung Sik Cho et al., Scientific Reports (2020) 10:346 (Jan. 15, 2020.).

Ag-functionalized SnO2 Nanowires Based Sensor for NO2 Detection at Low Operating Temperature, Myung Sik Choi et al., J. Microelectron. Packag. Soc., 27(2), 11-17 (Jun. 19, 2020.).

Aerosol assisted chemical vapour deposition of gas sensitive SnO2 and Au-functionalised SnO2 nanorods via a non-catalysed vapour solid (VS) mechanism, Stella Vallejos et al., Scientific Reports | 6:28464 (Jun. 23, 2016.).

English translation of "Ag-functionalized SnO2 Nanowires Based Sensor for NO2 Detection at Low Operating Temperature, Myung Sik Choi et al., J. Microelectron. Packag. Soc., 27(2), 11-17 (Jun. 19, 2020.)".

\* cited by examiner

SnO2  TIN DIOXIDE  150.709

| Phase | T [K] | C$_p$ | S | -(G-H298)/T | H | H-H298 | G | ΔH$_f$ | ΔG$_f$ | log K$_f$ |
|---|---|---|---|---|---|---|---|---|---|---|
| | | | J/(K·mol) | | | | kJ/mol | | | [ - ] |
| SOL | 298.15 | 52.594 | 52.342 | 52.342 | -580.823 | 0.000 | -596.423 | -580.823 | -520.000 | 91.102 |
| | 300.00 | 52.689 | 52.667 | 52.343 | -580.726 | 0.097 | -596.526 | -580.833 | -519.623 | 90.474 |
| | 400.00 | 60.999 | 68.847 | 54.496 | -575.082 | 5.741 | -602.621 | -580.950 | -499.187 | 65.187 |
| | 500.00 | 67.397 | 83.202 | 58.827 | -568.635 | 12.188 | -610.236 | -580.538 | -478.785 | 50.018 |
| | 600.00 | 73.425 | 96.106 | 63.363 | -561.549 | 19.274 | -619.213 | -586.565 | -457.197 | 39.803 |
| | 700.00 | 77.309 | 107.733 | 68.417 | -554.002 | 26.821 | -629.415 | -585.132 | -435.745 | 32.518 |
| | 800.00 | 80.094 | 118.348 | 74.875 | -546.124 | 34.699 | -640.723 | -583.438 | -414.517 | 27.065 |
| | 900.00 | 82.096 | 127.804 | 80.233 | -538.009 | 42.814 | -653.033 | -581.572 | -393.513 | 22.838 |
| | 1000.00 | 83.535 | 136.532 | 85.433 | -529.723 | 51.100 | -666.256 | -579.593 | -372.723 | 19.469 |
| | 1100.00 | 84.568 | 144.545 | 90.448 | -521.315 | 59.508 | -680.315 | -577.540 | -352.134 | 16.721 |
| | 1200.00 | 85.313 | 151.937 | 95.268 | -512.819 | 68.004 | -695.144 | -575.436 | -331.736 | 14.440 |
| | 1300.00 | 85.864 | 158.789 | 99.894 | -504.259 | 76.564 | -710.685 | -573.308 | -311.513 | 12.517 |
| | 1400.00 | 86.299 | 165.168 | 104.331 | -495.651 | 85.172 | -726.888 | -571.155 | -291.456 | 10.874 |
| | 1500.00 | 86.667 | 171.136 | 108.588 | -487.001 | 93.822 | -743.705 | -568.992 | -271.553 | 9.456 |
| | 1600.00 | 87.087 | 176.743 | 112.674 | -478.313 | 102.510 | -761.101 | -566.818 | -251.795 | 8.220 |
| | 1700.00 | 87.557 | 182.035 | 116.600 | -469.581 | 111.242 | -779.043 | -564.622 | -232.173 | 7.134 |
| | 1800.00 | 88.149 | 187.057 | 120.376 | -460.797 | 120.026 | -797.500 | -562.399 | -212.681 | 6.172 |

References

| Phase | H / S | C$_p$ |
|---|---|---|
| SOL | Tx1,Pa1 | Pa1 |

NANOCOMPOSITE COMPRISING TWO-DIMENSIONAL NANO THIN FILMS FORMED ON AU NANOPARTICLE SURFACE AND METHOD FOR MANUFACTURING SAME

CROSS-REFERENCE TO RELATED APPLICATION(S)

This application is based on and claims priority under 35 U.S.C. 119 to Korean Patent Application No. 10-2020-0088600, filed on Jul. 17, 2020, in the Korean Intellectual Property Office, the disclosure of which is herein incorporated by reference in its entirety.

TECHNICAL FIELD

Embodiments of the disclosure relate to an Au-embedded $SnO_2$ nanocomposite and a method for manufacturing the same, and more particularly, an Au-embedded $SnO_2$ nanocomposite, in which Au is adsorbed on a $SnO_2$ nanowire, and the Au-adsorbed $SnO_2$ nanowire is coated with a thin $SnO_{2-x}$ ($0 \leq x < 2$) thin film and a method for manufacturing the same using an FCVD process.

DESCRIPTION OF RELATED ART

Unlike bulky structures, nanostructures experience significant energy fluctuations and changes in conductivity even with a slight size variation. In particular, quantum-level nanostructures go through drastic changes in drastic electrical and optical properties regardless of their dimension and thus play a key role in various applications, such as display devices, solar cells or light detectors, photoelectrochemical cells, lasers, optical sensors, and bio imaging technology.

The concept of quantum means not only a very small size but also potential to make various morphological, compositional, structural, or functional changes. In a quantum structure, a slight difference may lead to significant changes in function, efficiency, or physicochemical limit. The concept of quantum may be interpreted as any form that may increase reaction sensitivity or speed.

Thus, although having the same size, quantum-sized materials may exhibit significantly different functions depending on what properties are given to the size.

To raise reaction efficiency while giving multiple functions, noble metal-adsorbed semiconductor nanocomposites have been widely used.

However, there is no technique to freely control nano-sized (quantum) structures with slight structural manipulation, nor is there research to obtain prominent outcomes by easily inducing a change in nano (quantum) units.

Thus, the inventors formed a peapod-shaped AU-embedded $SnO_2$ nanocomposite, in which Au particles are buried in a Sn-rich $SnO_2$ thin layer, by a new technique called flame chemical vapor deposition (FCVD). The inventors also analyzed and verified superiority in surface/interface reaction and differences in various gas sensing indexes as compared with conventional open-type nanocomposites. Embodiments of the disclosure may provide peapod-shaped nanocomposites in a simplified, comfortable, and efficient manner and may have applications in various sectors, such as switches, light emitting devices, batteries, capacitors, and nano emitters.

SUMMARY

According to an embodiment, a gold (Au)-embedded triple-layer $SnO_2$ nanocomposite comprises three layers of $SnO_2$—Au—$SnO_2$-x ($0<x<2$), wherein the Au is buried between the $SnO_2$ and $SnO_{2-x}$ ($0<x<2$) layers.

A $SnO_2$-x ($0<x<2$) nano-thin film may be formed on Au nanoparticles.

The $SnO_{2-x}$ ($0 \leq x < 2$) nano-thin film may have a thickness of 3 nm to 5 nm.

According to an embodiment, a method for manufacturing an Au-embedded triple-layer $SnO_2$ nanocomposite comprises putting organic materials containing Au and a metal salt on an $SnO_2$ nanowire and adsorbing the Au on the $SnO_2$ nanowire by instantly vaporizing the organic materials, except for the Au, by flame chemical vapor deposition (FCVD), wherein the Au-embedded triple-layer $SnO_2$ nanocomposite comprises three layers of $SnO_2$—Au—$SnO_2$-x ($0<x<2$), and wherein Au is buried between the $SnO_2$ and $SnO_{2-x}$ ($0<x<2$) layers.

An $SnO_2$-x ($0<x<2$) nano-thin film may be formed on Au nanoparticles.

The organic materials containing the Au and the metal salt may be $HAuCl_4 \cdot 4H_2O$ (l) and $(CH_3)_2CHOH$ (l), respectively.

The FCVD may include directly radiating a flame at 1200° C. to 1500° C. for 3 seconds to 7 seconds.

According to an embodiment, a gas sensor comprises an Au-embedded triple-layer $SnO_2$ nanocomposite including three layers of $SnO_2$—Au—$SnO_2$-x ($0<x<2$), with the Au buried between the $SnO_2$ and $SnO_{2-x}$ ($0<x<2$) layers.

A $SnO_2$-x ($0<x<2$) nano-thin film may be formed on Au nanoparticles.

The $SnO_{2-x}$ ($0<x<2$) nano-thin film may have a thickness of is 3 nm to 5 nm.

The gas sensor may comprise a substrate and an electrode disposed on the substrate. The Au-embedded triple-layer $SnO_2$ nanocomposite may be formed on an upper surface, a lower surface, or a side surface.

The disclosure may provide an AU-embedded $SnO_2$ nanocomposite that has three heterogeneous layers of Sn-rich $SnO_2$/Au/$SnO_2$ and two contact interfaces, unlike conventional Au-adsorbed $SnO_2$ nanocomposites which have two heterogeneous layers and one contact interface.

The disclosure may provide a method for manufacturing an AU-embedded $SnO_2$ nanocomposite that has three heterogeneous layers of Sn-rich $SnO_2$/Au/$SnO_2$ and two contact interfaces by flame chemical vapor deposition (FCVD).

According to the embodiments of the disclosure, the AU-embedded $SnO_2$ nanocomposite may meet both the spillover of the conventional Au-adsorbed $SnO_2$ nanocomposite and an increase in surface energy due to the Sn-rich $SnO_2$ nano thin film and a change in composition, as well as a change in conduction channel.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings, wherein:

FIGS. 9A and 9B illustrate the Gibbs free energy for Sn and $SnO_2$ in various temperature ranges including a synthesis temperature.

DETAILED DESCRIPTION

Figure 1:
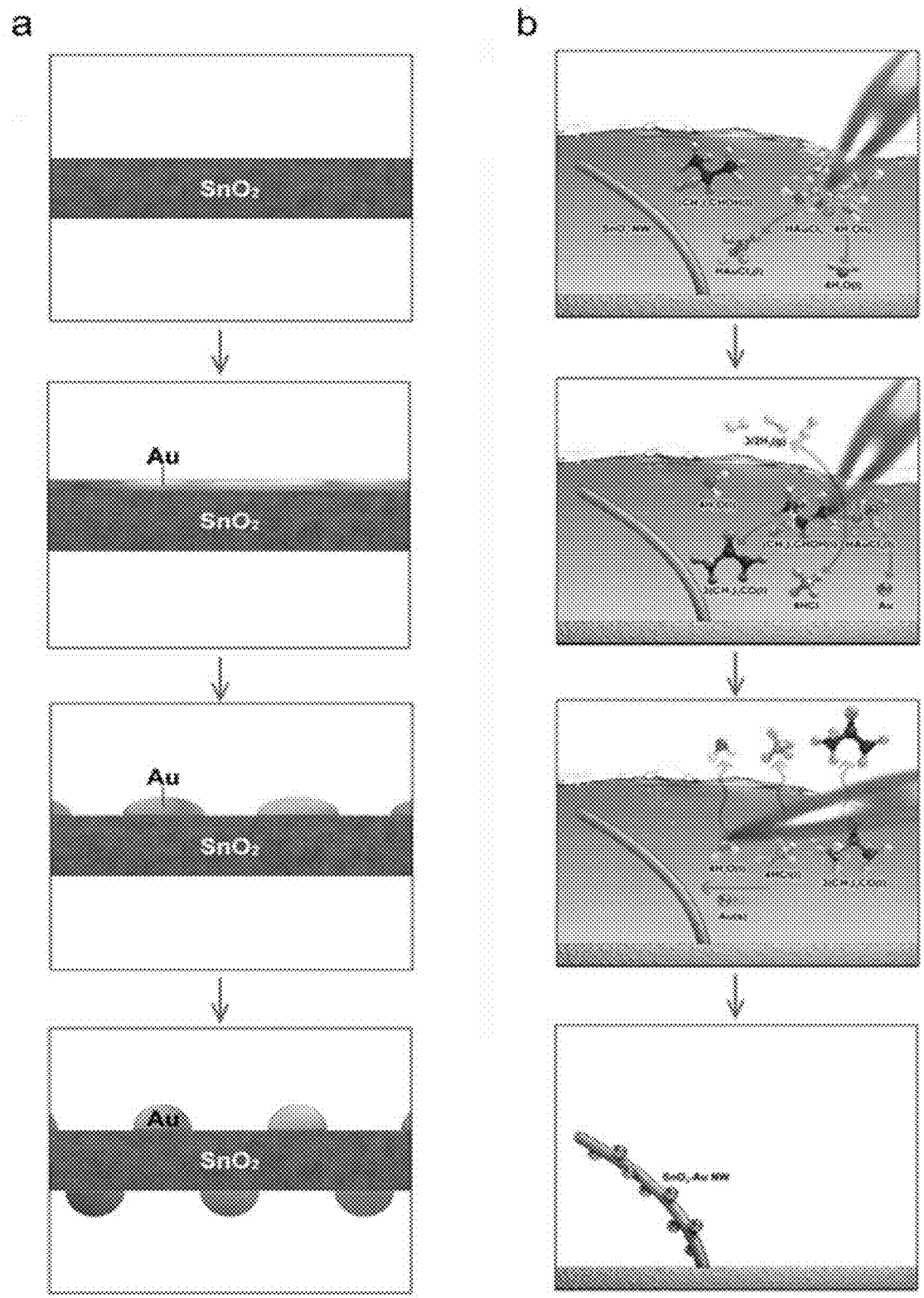
FIG. 1 illustrates a method for forming an Au-adsorbed $SnO_2$ nanocomposite according to the prior art and a method for forming an Au-adsorbed $SnO_2$ nanocomposite according to an embodiment.

Hereinafter, embodiments of the present invention are described in detail.

Unless defined otherwise, the terms used herein should be interpreted as understood by those of ordinary skill in the art to which this invention pertains.

No repetitive or duplicate description of the conventional art is given below.

According to an embodiment, a gold (Au)-embedded triple-layer $SnO_2$ nanocomposite comprises three layers of $SnO_2$—Au—$SnO_2$-x ($0<x<2$), wherein the Au is buried between the $SnO_2$ and $SnO_{2-x}$ ($0<x<2$) layers.

A $SnO_2$-x ($0<x<2$) nano-thin film may be formed on Au nanoparticles.

The $SnO_{2-x}$ ($0<x<2$) nano-thin film may have a thickness of 3 nm to 5 nm.

According to an embodiment, a method for manufacturing an Au-embedded triple-layer $SnO_2$ nanocomposite comprises putting organic materials containing Au and a metal salt on an $SnO_2$ nanowire and adsorbing the Au on the $SnO_2$ nanowire by instantly vaporizing the organic materials, except for the Au, by flame chemical vapor deposition (FCVD), wherein the Au-embedded triple-layer $SnO_2$ nanocomposite comprises three layers of $SnO_2$—Au—$SnO_2$-x ($0<x<2$), and wherein Au is buried between the $SnO_2$ and $SnO_{2-x}$ ($0<x<2$) layers.

An $SnO_2$-x ($0<x<2$) nano-thin film may be formed on Au nanoparticles.

The organic materials containing the Au and the metal salt may be $HAuCl_4.4H_2O$ (l) and $(CH_3)_2CHOH$ (l), respectively.

The FCVD may include directly radiating a flame at 1200° C. to 1500° C. for 3 seconds to 7 seconds.

According to an embodiment, a gas sensor comprises an Au-embedded triple-layer $SnO_2$ nanocomposite including three layers of $SnO_2$—Au—$SnO_2$-x ($0<x<2$), with the Au buried between the $SnO_2$ and $SnO_{2-x}$ ($0<x<2$) layers.

A $SnO_2$-x ($0<x<2$) nano-thin film may be formed on Au nanoparticles.

The $SnO_{2-x}$ ($0<x<2$) nano-thin film may have a thickness of is 3 nm to 5 nm.

The gas sensor may comprise a substrate and an electrode disposed on the substrate. The Au-embedded triple-layer $SnO_2$ nanocomposite may be formed on an upper surface, a lower surface, or a side surface.

The substrate may be a ceramic substrate, an alumina ($Al_2O_3$) substrate, a silicon (Si) substrate on which an insulating layer is deposited, or a silicon oxide ($SiO_2$) substrate.

The electrode may be an electrode of each or a combination of platinum (Pt), gold (Au), silver (Ag), nickel (Ni), copper (Cu), and titanium (Ti).

The electrode may include a first electrode and a second electrode spaced apart from each other to expose a sensing layer. The exposed sensing layer may be substantially a sensing area of the gas sensor.

The sensing layer may have a shape selected from the group consisting of a line pattern, a lattice shape, a curved shape, a cylindrical shape, a rectangular column shape, an inverted cone shape, a rectangular parallelepiped shape, a top shape, a cup shape, and a U shape on the electrode.

According to an embodiment, there is also provided an electrochemical device, such as a switch, a light emitting device, a battery, a capacitor, and a nano-emitter, including an Au-embedded triple-layer $SnO_2$ nanocomposite.

According to an embodiment, an embedded Au-adsorbed $SnO_2$ nanostructure was synthesized in seconds. It was identified that, unlike the conventional Au-adsorbed $SnO_2$ structure which includes two heterogeneous layers and one contact interface, the Au-embedded triple-layer $SnO_2$ nanocomposite, according to an embodiment, has a similar structure to a peapod structure but, distinctly therefrom, has a unique structure that includes three heterogeneous layers, i.e., an Sn-rich $SnO_2$ layer, an Au layer, and an $SnO_2$ layer, and two contact interfaces.

According to embodiments, the embedded Au-adsorbed $SnO_2$ nanostructure is synthesized using a new technique called flame chemical vapor deposition (FCVD), and a mechanism for forming Au-embedded $SnO_2$ is proposed.

According to embodiments, to figure out the effects of an AU-embedded $SnO_2$ nanocomposite, changes in conduction channel, an increase in surface energy due to the nano thin film and a change in composition, and the spillover of the conventional nanocomposite were verified using gas sensing.

The disclosure is now described in further detail in connection with embodiments thereof. The embodiments herein are provided merely for illustrating the disclosure, and it will be apparent to those of ordinary skill in the art that the scope of the disclosure is not interpreted as limited thereby or thereto.

FIG. 1 illustrates a method for forming an Au-adsorbed $SnO_2$ nanocomposite according to the prior art and a method for forming an Au-adsorbed $SnO_2$ nanocomposite according to an embodiment, in which a shows a nanocomposite formed by thermal evaporation-based $SnO_2$ synthesis, followed by continuously performing Au sputtering and thermal treatment, and b shows a nanocomposite formed by thermal evaporation-based $SnO_2$ synthesis, followed by continuously performing FCVD on Au-containing organic materials and a metal sault.

Figure 2:
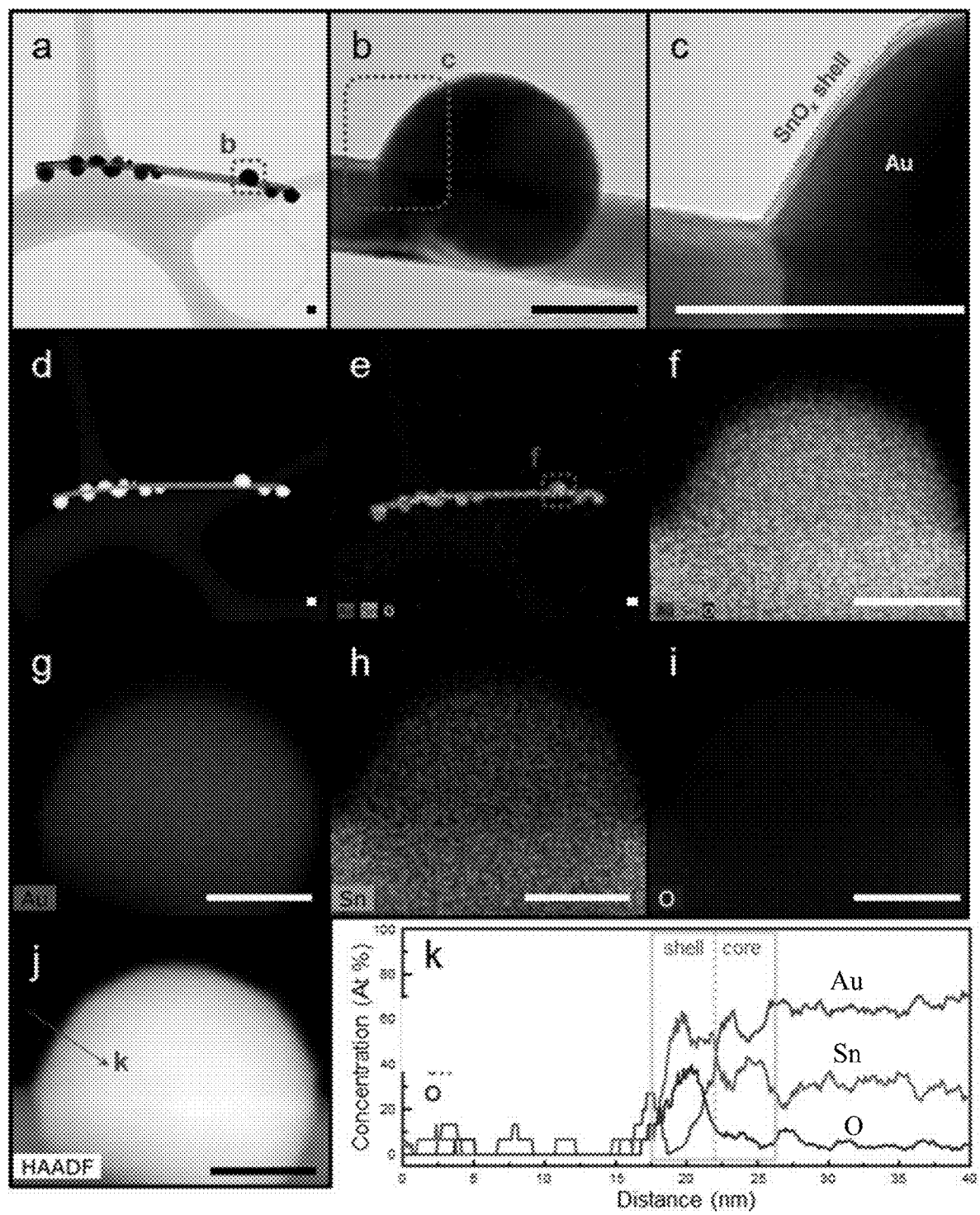
FIG. 2 illustrates transmission electron microscopy (TEM) images and composition analysis for an AU-embedded $SnO_2$ nanocomposite synthesized by the FCVD according to an embodiment.

FIG. 2 illustrates transmission electron microscopy (TEM) images and composition analysis for an AU-embedded $SnO_2$ nanocomposite synthesized by the FCVD according to an embodiment, in which a is a low-magnification image for a conventional nanocomposite sample, b is an image for the boundary between an Au nanoparticle and an $SnO_2$ nanowire, c is a high-magnification image of an Sn-rich $SnO_2$ nano thin film, d is a low-magnification STEM image for a, e is an image of Au, Sn, and O in portions of an AU-embedded $SnO_2$ nanocomposite, f is an image for all the elements at the Au—$SnO_2$ boundary (Sn and O both are detected from the thin film on the Au nanoparticle), g is an image showing a distribution of Au at the Au—$SnO_2$ boundary, h is an image showing a distribution of Sn at the Au—$SnO_2$ boundary, i is an image showing a distribution of O at the Au—$SnO_2$ boundary, j is a STEM HAADF image of Au buildup on $SnO_2$, and k is an image showing changes in composition from the outermost part of the Au particle to the center along the direction indicated with the arrow of j (no element is detected up to the nanoparticle, and Sn and O are more detected than Au at the surface, and Au is most detected in the deeper portion).

Figure 3:
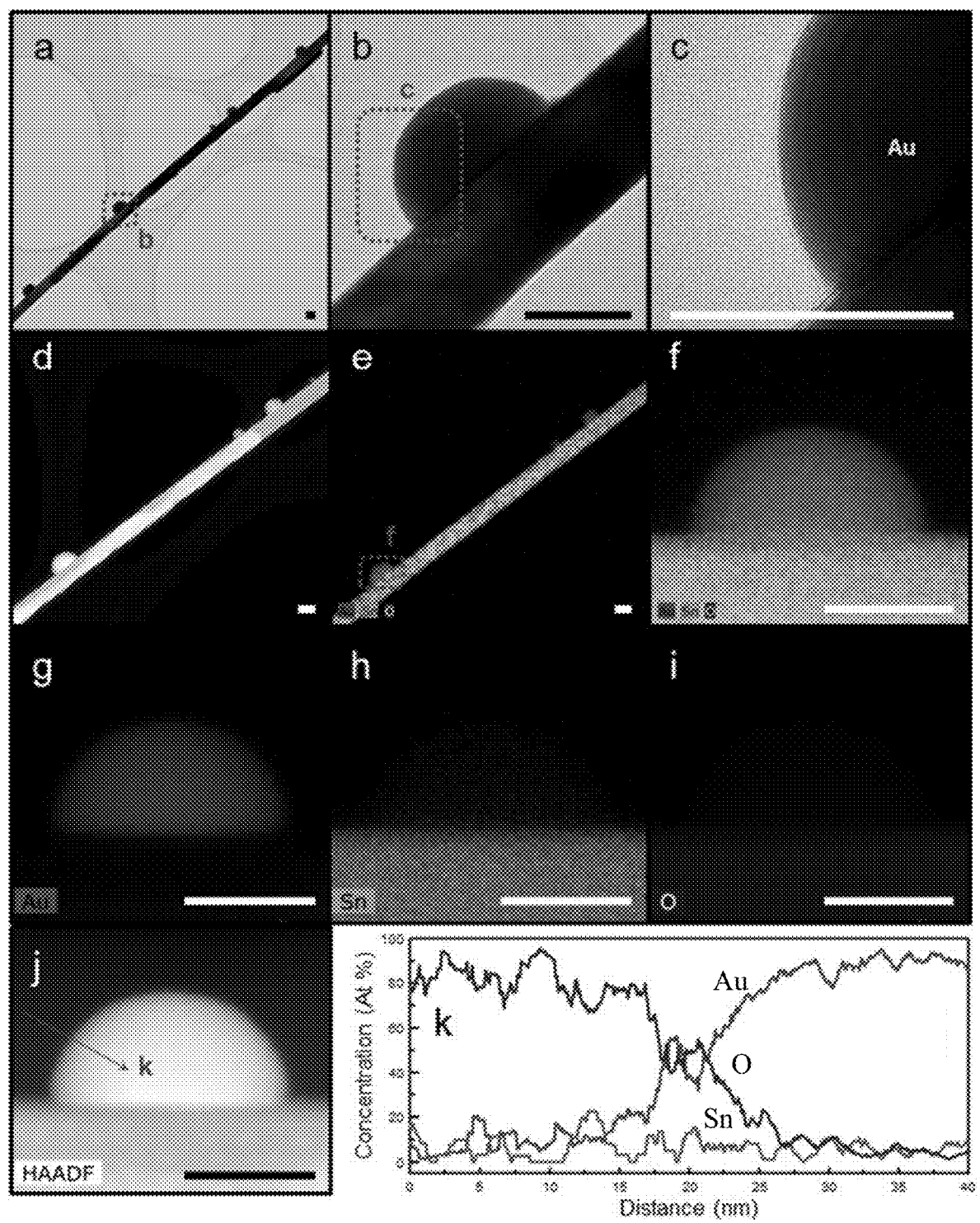
FIG. 3 illustrates TEM images and composition analysis for an Au-adsorbed $SnO_2$ nanocomposite synthesized by the conventional sputtering method.

FIG. 3 illustrates TEM images and composition analysis for an Au-adsorbed $SnO_2$ nanocomposite synthesized by the conventional sputtering method, in which a is a low-magnification image of a conventional nanocomposite sample, b is an image of the boundary between the Au nanoparticle and the $SnO_2$ nanowire, c is a high-magnification image for Au particle with no layer formed thereon, d is a low-magnification STEM image of a, e is an image of Au, Sn, and O in portions of an AU-embedded $SnO_2$ nanocomposite, f is an image for all the elements at the Au—$SnO_2$ boundary (no other element than Au is detected on the Au nanoparticle), g is an image showing a distribution of Au at the Au—$SnO_2$ boundary, h is an image showing a distribution of Sn at the Au—$SnO_2$ boundary, i is an image showing a distribution of O at the Au—$SnO_2$ boundary, j is a STEM HAADF image of Au buildup on $SnO_{2-x}$ and k is an image showing changes in composition from the outermost part of the Au particle to the center along the direction indicated with the arrow of j (no element is detected up to the nanoparticle and, at the surface, Au is more detected, and the other elements, i.e., Sn and O, are hardly detected).

Figure 4:
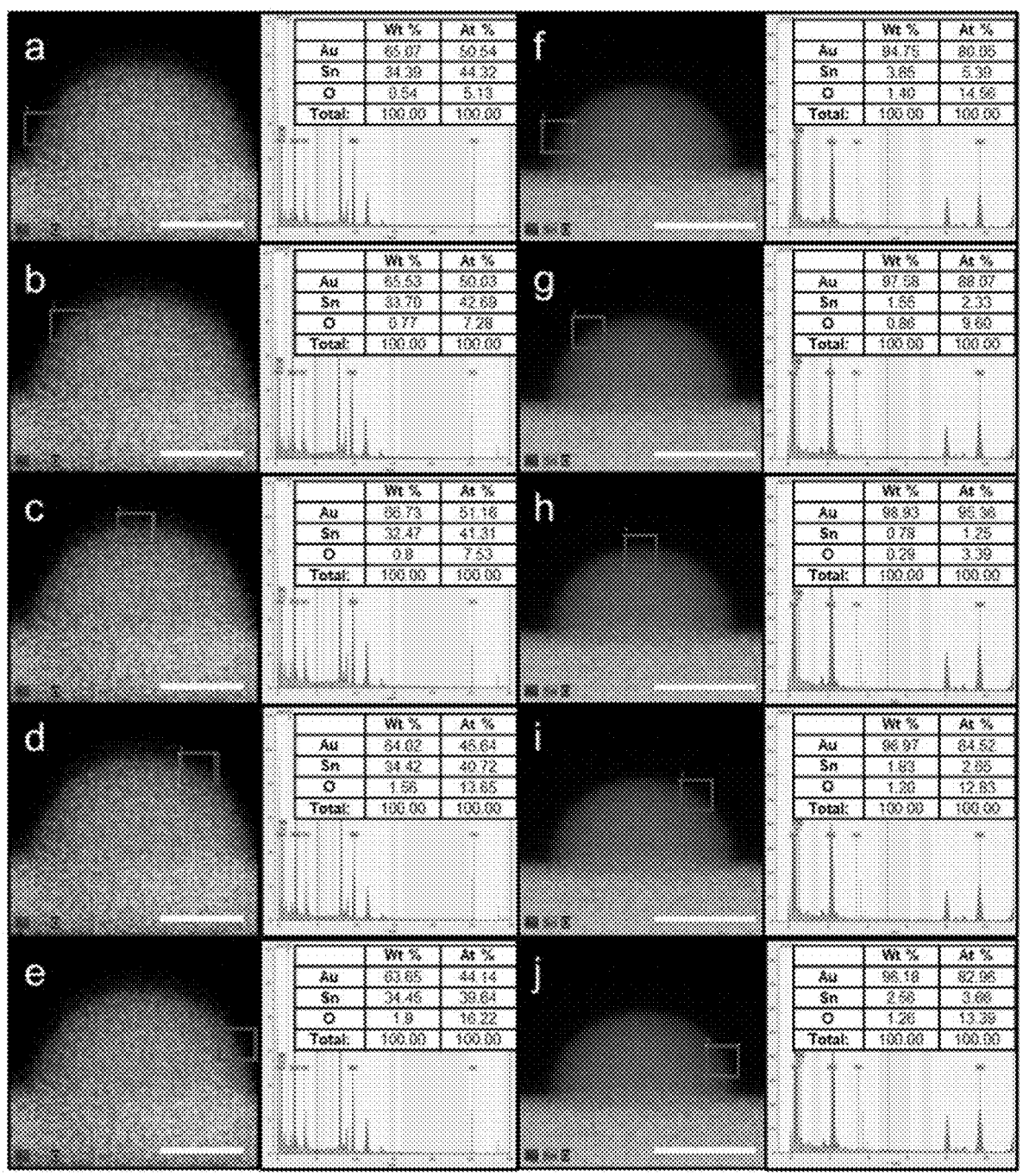
FIG. 4 illustrates results of component analysis at the surface of Au nanocomposites for Au-adsorbed $SnO_2$ nanocomposites synthesized by the FCVD according to an embodiment and by the conventional method.

FIG. 4 illustrates results of component analysis at the surface of Au nanocomposites for Au-adsorbed $SnO_2$ nanocomposites synthesized by the FCVD according to an embodiment and by the conventional method, in which a to e show that Sn and O, constituting the Sn-rich $SnO_2$ thin film, both are detected on the surface of the Au nanoparticle, regardless of position, and f to j show that Sn and O are not detected on the surface of the Au nanoparticle regardless of position.

Figure 5:
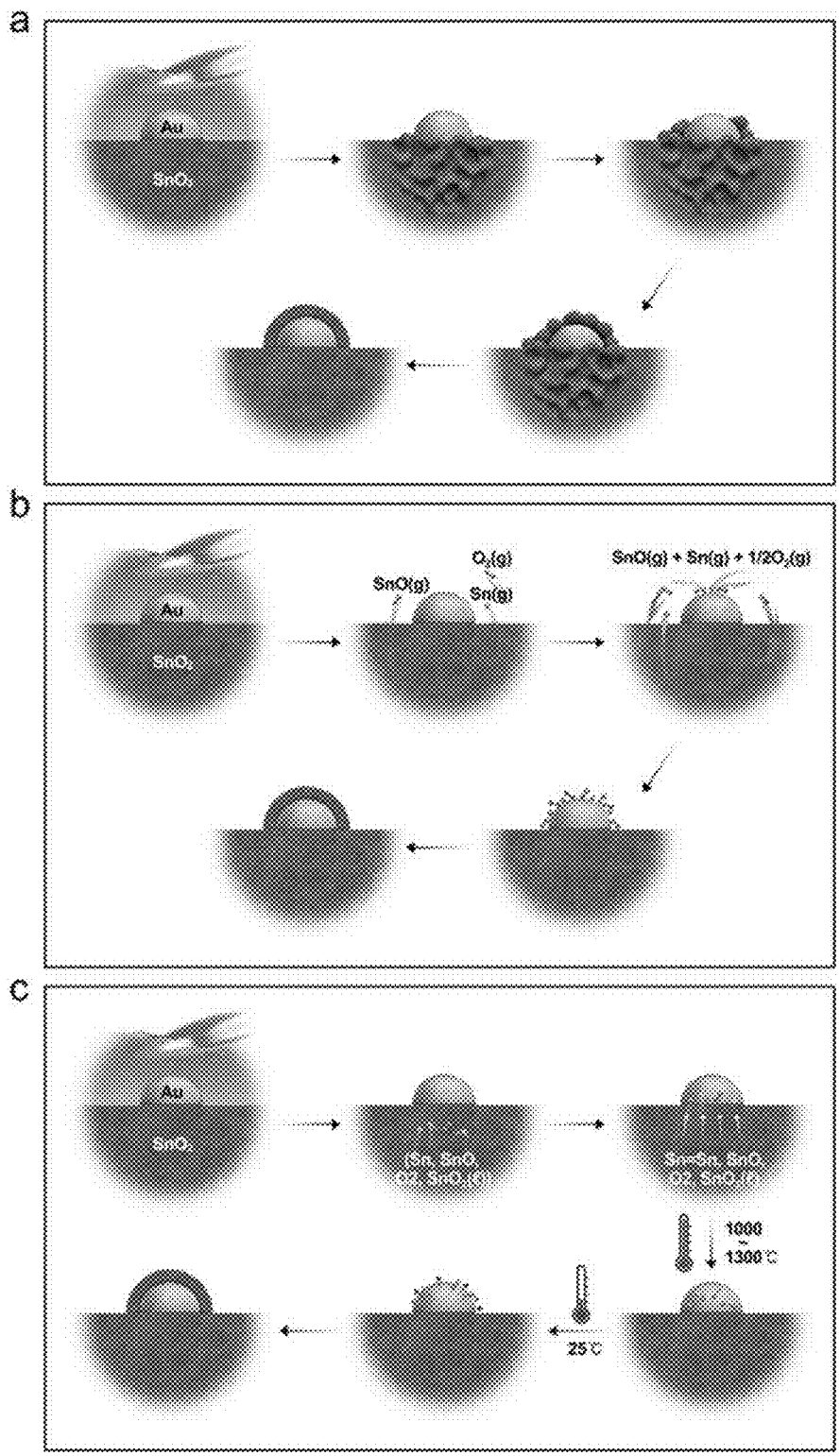
FIG. 5 illustrates three different scenario cases in which AU-embedded $SnO_2$ is formed.

FIG. 5 illustrates three different scenario cases in which AU-embedded $SnO_2$ is formed.

Figure 6:
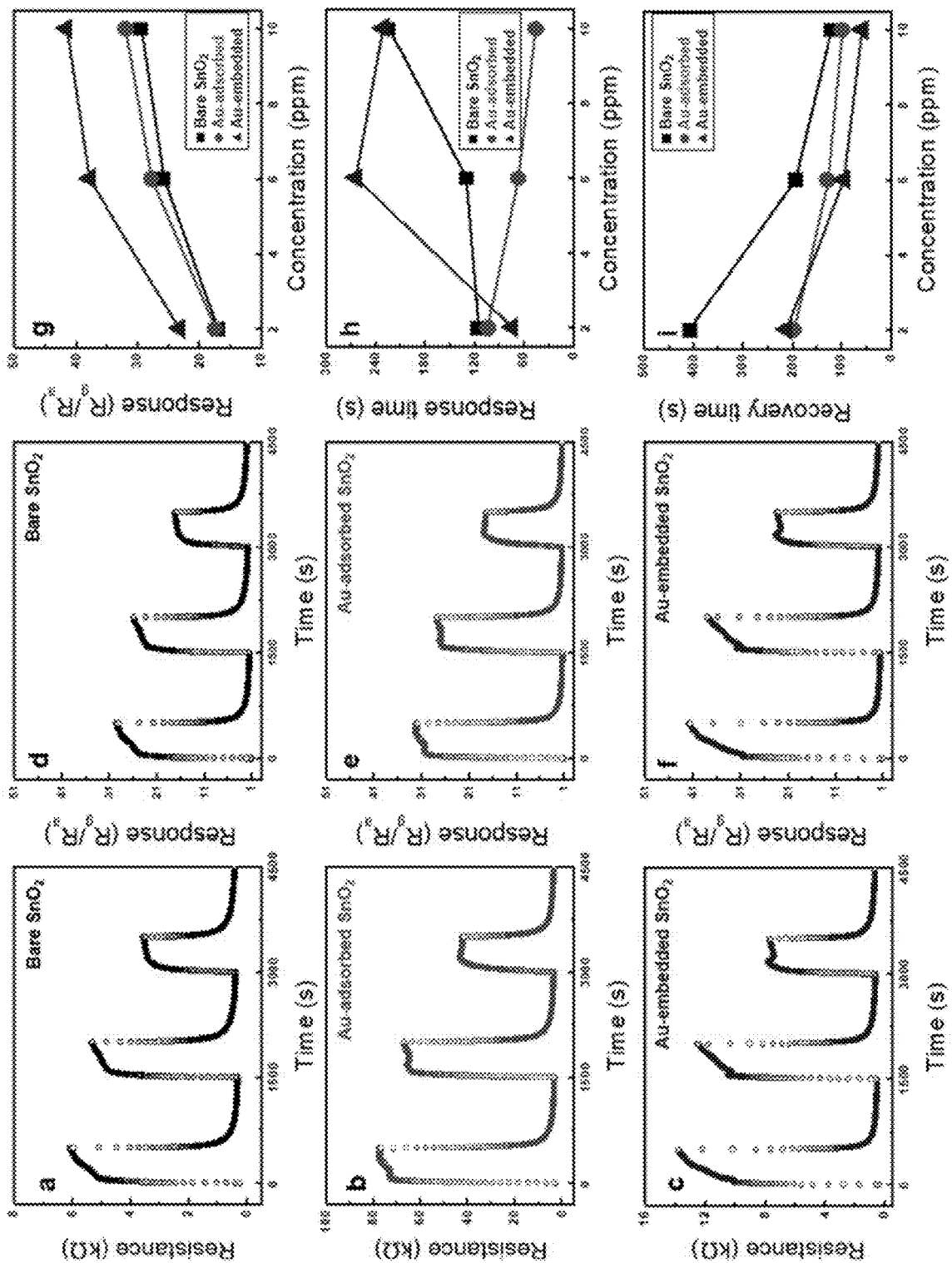
FIG. 6 illustrates graphs showing the gas sensing indexes of three different samples with different surfaces, according to different $NO_2$ gas concentrations, obtained at the same processing temperature, e.g., 100° C.

FIG. 6 illustrates graphs showing the gas sensing indexes of three different samples with different surfaces, according to different $NO_2$ gas concentrations, obtained at the same processing temperature, e.g., 100° C., in which a, b, and c show changes in resistance over time for bare SnO, Au-adsorbed $SnO_{2-x}$ and AU-embedded $SnO_{2-x}$ respectively, d, e, and f show changes in response over time for bare SnO, Au-adsorbed $SnO_{2-x}$ and AU-embedded $SnO_{2-x}$ respectively, and g, h, and i show the results of comparison between bare $SnO_{2-x}$ Au-adsorbed $SnO_{2-x}$ and AU-embedded $SnO_{2-x}$ for response, response time, and recovery time, respectively.

Figure 7:
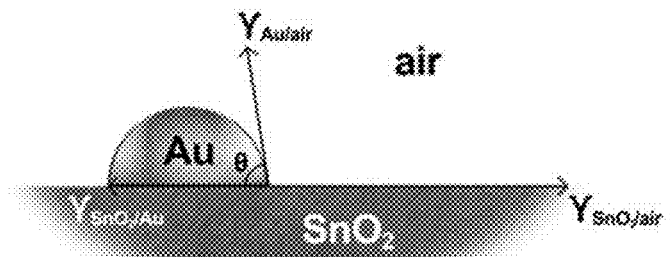
FIG. 7 illustrates methods for obtaining surface energy for an Au-adsorbed $SnO_2$ nanocomposite and an AU-embedded $SnO_2$ nanocomposite and comparison therebetween.
Figure 7:
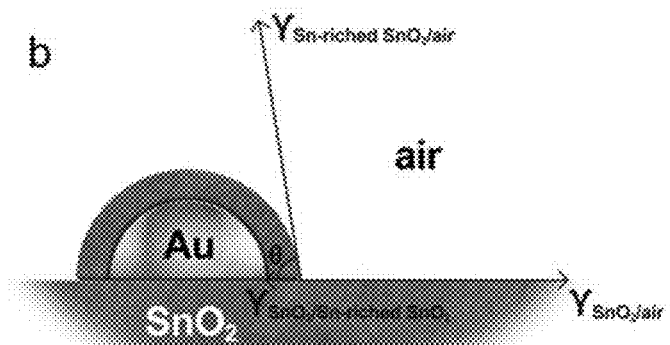
Figure 7:
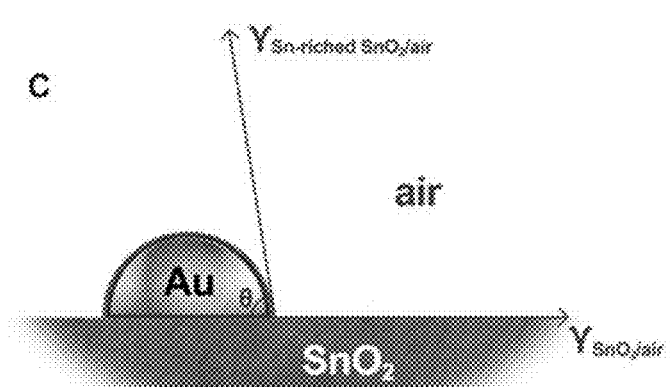

FIG. 7 illustrates methods for obtaining surface energy for an Au-adsorbed $SnO_2$ nanocomposite and an AU-embedded $SnO_2$ nanocomposite and comparison therebetween, in which a shows energy equilibrium of three types of surface energy when an Au nanoparticle is formed on an $SnO_2$ nanowire, b shows energy equilibrium of three different types of surface energy when an Sn-rich $SnO_2$ thin film is formed on the Au nanoparticle, and c shows energy equilibrium of three different types of surface energy when an Sn-rich $SnO_2$ thin film is formed on the Au nanoparticle and its thickness is close to 0 (i.e., when the nano thin film is extremely thin).

Figure 8:
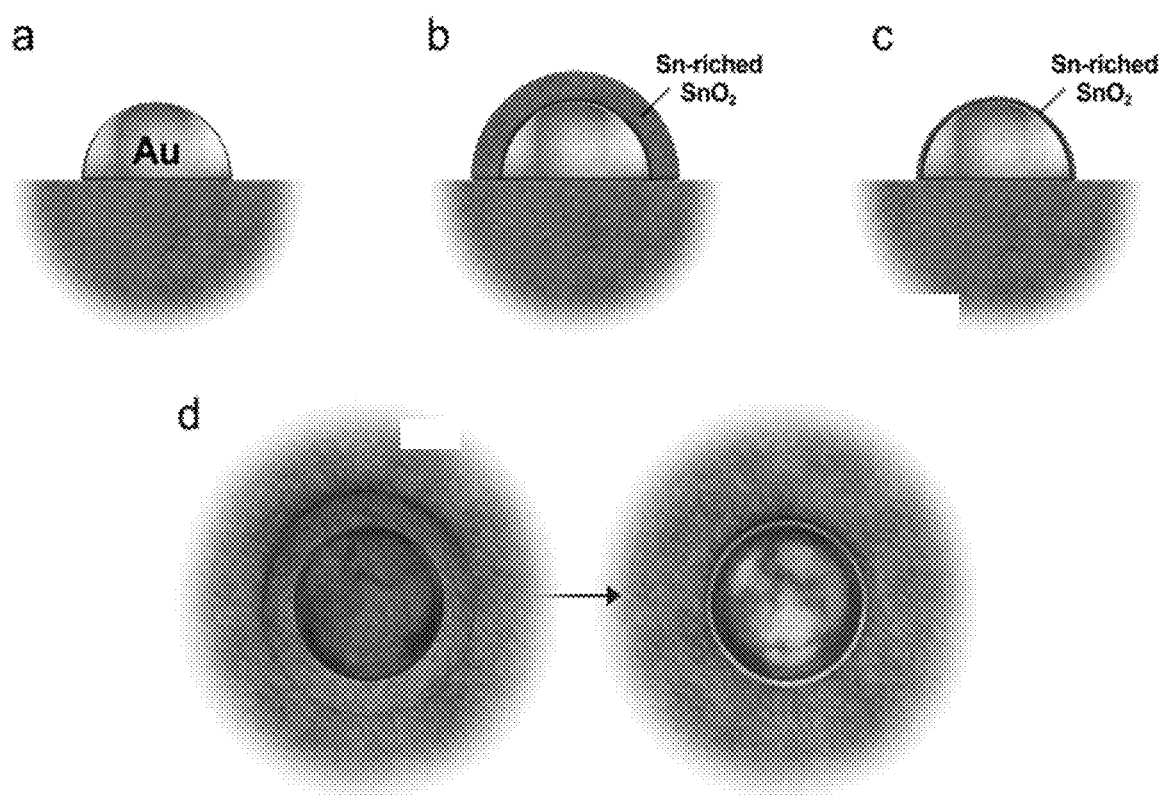
FIG. 8 illustrates an example in which as the cross-sectional area of an Sn-rich $SnO_2$ thin film surrounding an Au particle decreases, the surface energy of the Sn-rich $SnO_2$ thin film increases.

FIG. 8 illustrates an example in which as the cross-sectional area of an Sn-rich $SnO_2$ thin film surrounding an Au particle decreases, the surface energy of the Sn-rich $SnO_2$ thin film increases, in which a is a cross-sectional view of Au-adsorbed $SnO_2$, b is a cross-sectional view of Sn-rich $SnO_2$ formed on an Au nanoparticle, c is a cross-sectional view of an ultra-thin Sn-rich $SnO_2$ film on an Au nanoparticle, and d is a plan view of Sn-rich $SnO_2$ formed on an Au nanoparticle, according to the thickness.

Figure 9A:
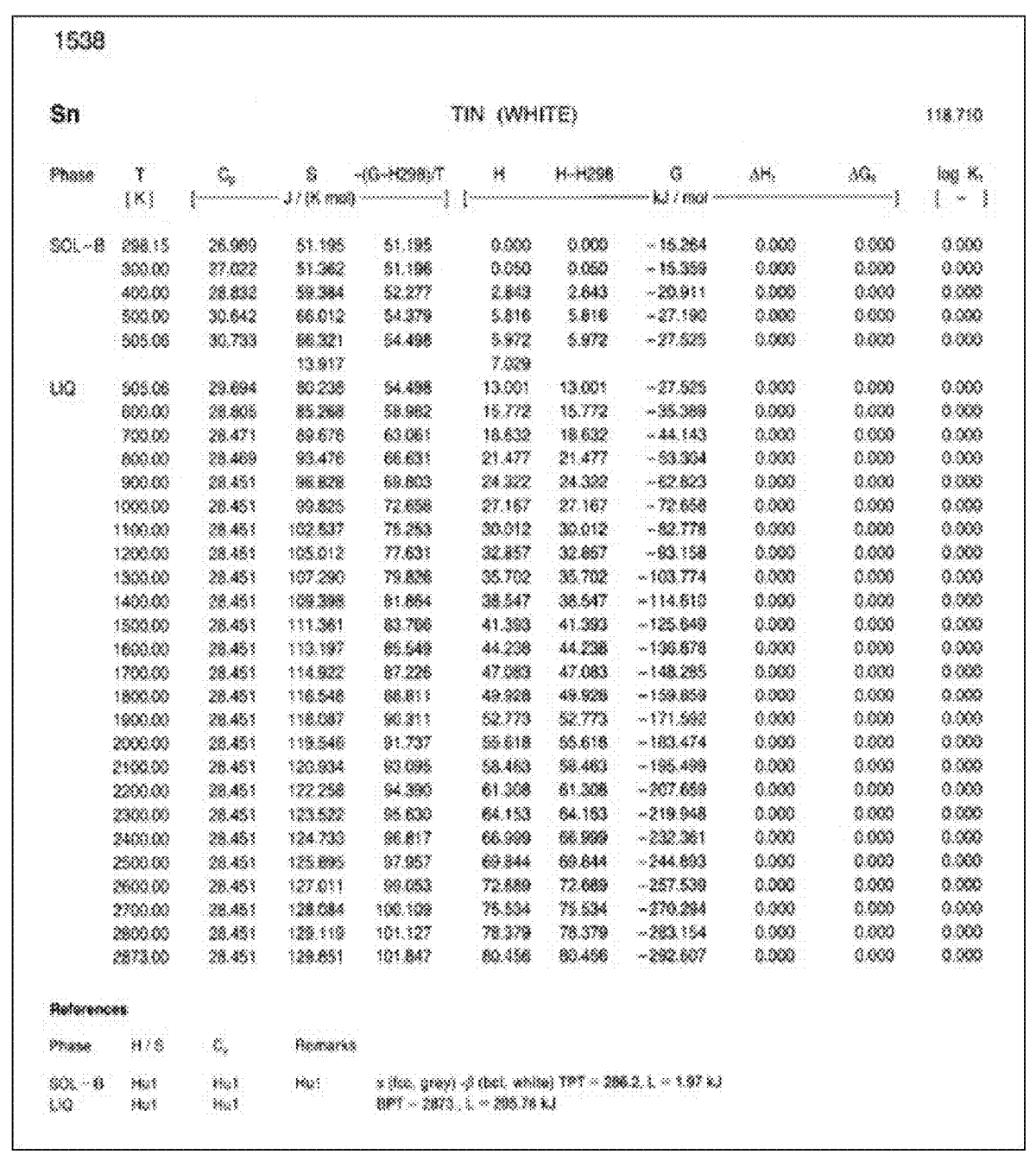

FIGS. 9A and 9B illustrate the Gibbs free energy for Sn and $SnO_2$ in various temperature ranges including a synthesis temperature, in which a is a table showing the Gibbs free energy for Sn, and b is a table showing the Gibbs free energy for $SnO_2$.

Figure 10:
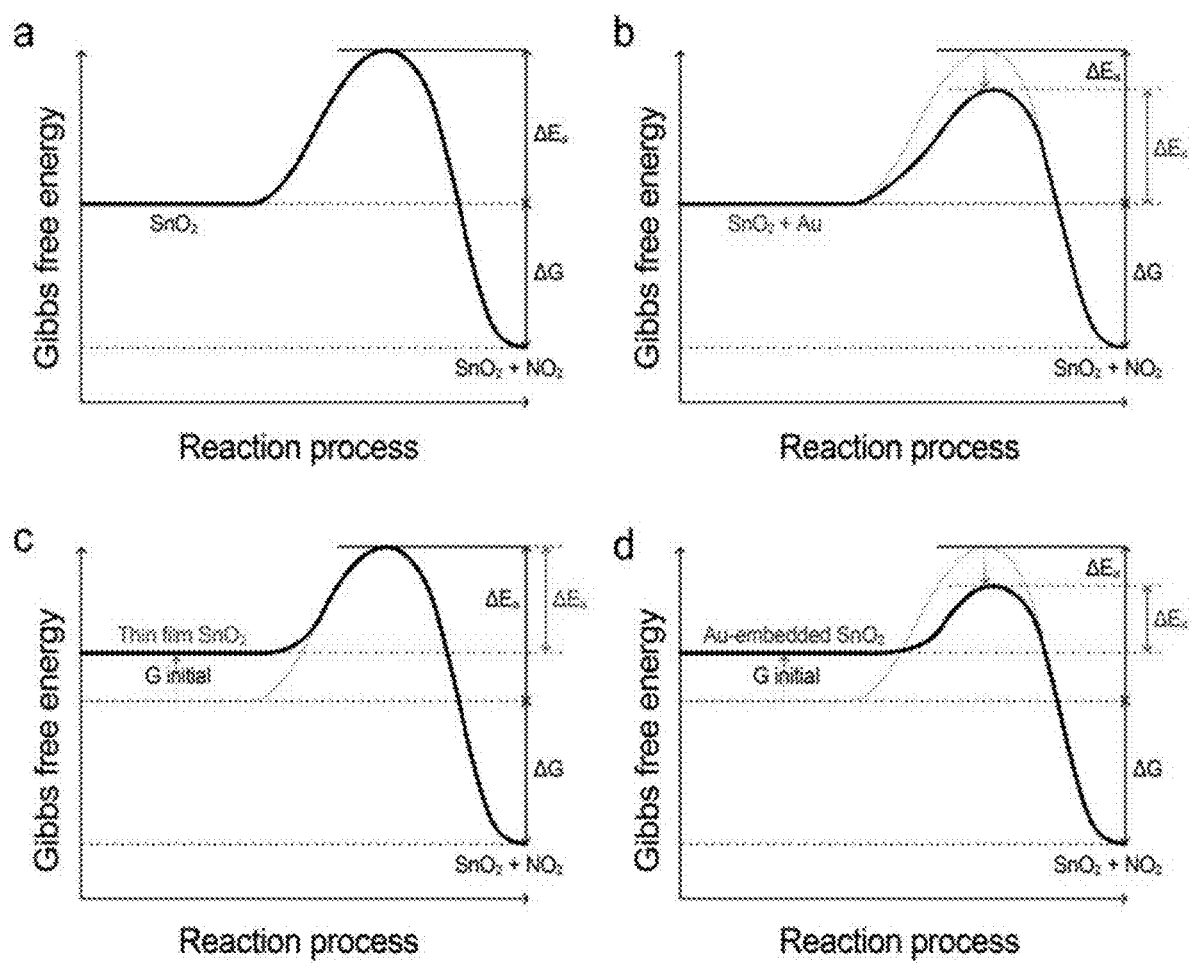
FIG. 10 illustrates graphs showing changes in the Gibbs free energy in an $NO_2$ gas adsorption reaction when the state of the surface of an Au—$SnO_2$ nanocomposite is changed.

FIG. 10 illustrates graphs showing changes in the Gibbs free energy in an $NO_2$ gas adsorption reaction when the state of the surface of an Au—$SnO_2$ nanocomposite is changed, in which a is a graph showing changes in Gibbs free energy when $NO_2$ is adsorbed to the surface of $SnO_2$, b is a graph showing changes in Gibbs free energy when $NO_2$ is adsorbed after Au nanoparticles are formed on the surface of $SnO_2$, c is a graph showing changes in Gibbs free energy when $NO_2$ is adsorbed after a thin $SnO_2$ surface is formed or a composition change to Sn is made, and d is a graph showing changes in Gibbs free energy when $NO_2$ is adsorbed after Au nanoparticles are formed on the surface of $SnO_2$ and a thin Sn-rich $SnO_2$ surface is formed on the Au nanoparticles.

<Embodiment 1> Growth or Synthesis of $SnO_2$ Nanowires

A 3 nm-thick Au layer was deposited on a washed alumina substrate using direct current (DC) sputtering. The DC sputtering was performed under the following conditions: a current of 10 mA, a sputtering time of 1 minute, a degree of vacuum of $4 \times 10^{-5}$ mTorr, Ar as a working gas, and room temperature. 1 g of Sn powder was spread evenly in an alumina boat, and the alumina substrate was placed on the alumina boat, with the Au-deposited surface facing the Sn powder. Thereafter, the temperature was raised to 900° C. at a temperature increase rate of 10° C./min and then left for 1 hour. Oxygen and argon in a ratio of 1:9 were maintained at a gas pressure of 2 Torr.

<Embodiment 2> Synthesis of Embedded Catalyst 0.23 g of Gold Chloride hydrate 99.995% ($HAuCl)_4 \cdot 4H_2O$) and 10 g of 2-propanol 99.5% (($CH_3)_2CHOH$) were put in a beaker and mixed for 30 min using a stirrer. Then, 3 ml of the mix was dropped on the $SnO_2$ nanowire grown according to embodiment 1 above, and a flame was directly radiated to the $SnO_2$ nanowire at 1300° C. for 5 seconds using an FCVD machine. The process was carried out at room temperature and atmospheric pressure.

<Embodiment 3> Synthesis of Open Catalyst

A 3 nm-thick Au layer was deposited on the $SnO_2$ nanowire grown according to embodiment 1 above, using DC sputtering. The same sputtering conditions as those of embodiment 1 were used. Thereafter, heat treatment was performed in an Ar atmosphere at 500° C. for 2 hours.

<Embodiment 4> Property Analysis

A sample was analyzed for its shape and composition, using a transmission electron microscope (TEM, Talos F200X, FEI) and an energy dispersive X-ray spectroscope (EDS, Talos F200X, FEI), respectively.

<Embodiment 5> Gas Detection Test

A sensing device was prepared by depositing a 300 nm-thick Au layer on interdigitated electrodes on a sensing material synthesized on an alumina substrate, using DC sputtering. The flow rate of all the gases used in this experiment was 500 sccm. Response was set as Rg/Ra for oxidizing gas and Ra/Rg for reducing gas, where Ra is the resistance when the air flows, and Rg is the resistance when a toxic gas flows. Response time was set as the time taken for the reaction to be 90% done after saturation made by flowing the toxic gas. Recovery time was set as the time taken for it to be 90% recovered by flowing sufficient air after the toxic gas reaction.

<Experimental Example 1> Comparison Between Au-Adsorbed $SnO_2$ Nanocomposite According to an Embodiment and Au-Adsorbed $SnO_2$ According to the Prior Art <1-1> Forming Processes In one process, an Au layer was formed, by physical sputtering, on the surface of a $SnO_2$ nanowire pre-formed by conventional thermal evaporation, followed by post-thermal treatment to form island-shaped Au nanoparticles, and adsorbed to $SnO_2$, as illustrated in FIG. 1A.

In another process, an SnO nanowire previously formed by conventional thermal evaporation was put in organic materials, such as $HAuCl_4 \cdot 4H_2O$ (l) and a metal salt, e.g., $(CH_3)_2CHOH$ (l), and then, all the organic materials, except for Au, were instantly vaporized by a direct energy injection method, such as flame chemical vapor deposition (FCVD), so that only Au was adsorbed on $SnO_2$, as illustrated in FIG. 1B.

<1-2> Comparison of Microstructures

The two nanocomposites prepared by the forming processes described above in connection with <1-1> Forming processes exhibited slight differences in components. Comparison as to TEM data was made between AU-embedded $SnO_2$ prepared by FCVD, as illustrated in FIG. 2, and Au-adsorbed $SnO_2$ prepared by the conventional method, as illustrated in FIG. 3.

a to c of FIG. 2 depict the results of observation of a typical Au-adsorbed $SnO_2$ sample from a low to high magnification. It was observed that the $SnO_2$ nanowire has Au nanoparticles having a size ranging from about 80 nm to about 120 nm. This morphology may also be observed from the conventional Au-adsorbed $SnO_2$ nanocomposite (as illustrated in a to c of FIG. 3) obtained using thermal evaporation and sputtering and thus makes no difference.

d and e of FIG. 2 depict the composition of the AU-embedded $SnO_2$ prepared by FCVD, and it may be identified therefrom that the AU-embedded $SnO_2$ prepared by FCVD has a different composition from the conventional Au-adsorbed $SnO_2$ as illustrated in d and e of FIG. 3. In other words, the Au particles of the conventional Au-adsorbed $SnO_2$ include only particles of Au (see e of FIG. 3) whereas the AU-embedded $SnO_2$ prepared by FCVD has Au particles mixed with Sn and O (see e of FIG. 2). Such differences in composition may be more clearly shown from f to i of FIG. 2 and f to i of FIG. 3. f of FIGS. 2 and 3 show all the components of the Au nanoparticles, and it may be identified therefrom that all of the Au, Sn, and O components are mixed together in the AU-embedded $SnO_2$ prepared by FCVD whereas only Au is detected from the Au-adsorbed $SnO_2$ prepared by the conventional method. Such difference may be further clarified by identifying the presence or absence of the individual components as illustrated in g to i of FIG. 2 and g to i of FIG. 3. It may be identified that the AU-embedded $SnO_2$ prepared by FCVD has an Sn-rich $SnO_2$ ($SnO_x$) thin film formed on the Au nanoparticles as shown in c of FIG. 2. The results of composition analysis using high-angle annular dark-field imaging (HAADF) (see j of FIGS. 2 and 3) reveal that the AU-embedded $SnO_2$ prepared by FCVD is divided into a core of Au and a shell on the core, Sn and O are detected from the shell, and differences in concentration between Au and the other components (i.e., Sn and O) are not significant as shown in k of FIG. 2. In contrast, according to the conventional method, it is difficult to identify a core and a shell separated from each other, and a significant difference in concentration is shown between Au and the other components. Thus, it may be concluded that a thin Sn-rich $SnO_2$ layer is formed on the Au particles by FCVD. Although the two samples look similar, forming such a nano-sized thin film on the Au catalyst may not only make a structural difference between the two samples but also contribute to a significant enhancement in efficiency in applications (e.g., gas sensing-related surface reaction), which may not be achieved in the conventional art. It may be identified from the EDX results as shown in FIG. 4 that Sn-rich $SnO_2$ is formed on the entire surface, rather than only a portion of the surface, of the semi-spheric Au nanoparticles formed by FCVD.

<1-3> Morphological Comparison

Morphologically, the conventional Au-adsorbed $SnO_2$ simply consists of two layers of Au and $SnO_2$ (see f to k of FIG. 3) whereas the Au-adsorbed $SnO_2$ synthesized by FCVD is composed of three layers of Sn-rich $SnO_2$—Au—$SnO_2$ (see f to k of FIG. 2). In other words, a thin Sn-rich SnO layer is further formed along the surface of the Au particles, so that the Au particles are buried between the Sn-rich $SnO_2$ layer and the $SnO_2$ layer, forming a pea pod shape.

According to an embodiment, by adopting a new quick (e.g., within five seconds) process (i.e., FCVD) distinguished from conventional processes, it is possible to easily form such pea pod structures. It is also possible to allow no, or a thicker Sn-rich $SnO_2$ layer, to be formed on the Au particles by adjusting the processing time. In other words, the FCVD itself may instantly and freely change the structure of nanomaterials within a short time, thereby allowing for easier addition of various functions according to purposes or usages. As described above, the two samples, i.e., one according to the FCVD according to an embodiment and the other according to the conventional art, albeit looking similar in nanostructure, have completely different structures in a more microscopical aspect.

<Experimental Example 2> Analysis of the Mechanism of Forming AU-Embedded $SnO_2$ An analysis of the mechanism in which the FCVD generates AU-embedded $SnO_2$ was carried out. The following scenario cases were considered.

(1) If high-temperature thermal energy ranging from about 1000° C. to 1300° C. is instantly applied, in an atmosphere of organic materials and a metal salt, to an Au-adsorbed $SnO_2$ nanocomposite previously formed by thermal evaporation, relatively more energy is transferred to the Au and $SnO_2$ interface and turns the $SnO_2$ layer into a liquid state. In such a case, the Au nanoparticles may be submerged and enveloped by the molten $SnO_2$ layer which may then harden quickly. However, this case is less likely because $SnO_2$ would be vaporized by the high thermal energy from FCVD (a of FIG. 5 illustrates case (1)).

(2) If high thermal energy is applied to a preformed Au-adsorbed $SnO_2$ nanocomposite, $SnO_2$ may be decomposed as follows: $SnO_2(s)=SnO(g)+\frac{1}{2}O_2(g)$ or $SnO_2(s)=Sn(l)+O_2(g)$. In other words, vaporized (sublimated) SnO and $O_2$, or Sn and $O_2$, are adsorbed onto the surface of the Au particles, leading to a likelihood of forming Sn-based $SnO_2$. This may be so considered because such reversible reactions occur between 1000° C. and 1300° C., which are a range of temperatures of the process. However, this case is less likely because all of Sn, SnO, and $O_2$ vaporized (sublimated) are required to depart from the Au and $SnO_2$ layer and then be adsorbed back (b of FIG. 5 illustrates case (2)).

(3) As the temperature rises at the interface between Au and $SnO_2$ in the Au-adsorbed $SnO_2$ preformed at room temperature, due to application of high thermal energy, the limit to the solid solubility of Au with $SnO_2$ may increase. Thus, Sn, SnO, $O_2$, $SnO_{2-x}$ or whichever, in the $SnO_2$ layer influenced by the high thermal energy may be solid-soluble into Au and, as such spread continues, the solid solubility of Au may be supersaturated. If the temperature decreases, the Sn, SnO, and $SnO_2$ components are ejected out of the surface of the Au particles, so that the Au particles are buried therein, like peas in a pod. Due to the supersaturation at the high temperature as well as the solubility limit reduced as the temperature of Au decreases after the processing time, the Au particles continues to spit out the Sn-based elements. In other words, Sn-based $SnO_2$ surrounding the Au particles may be a result of precipitation that occurs because Au fails to accommodate the Sn-based elements. Scenario case (3) not only coincides with supersaturation in the VLS mechanism regarding nanostructure formation and growth, but also has a much higher chance of correctly describing the mechanism than scenario cases (1) and (2) described above (c of FIG. 5 illustrates case (3)).

<Experimental Example 3> Comparison in Surface/Interface Response to Gas Between Au-Adsorbed $SnO_2$ According to an Embodiment and Au-Adsorbed $SnO_2$ According to the Prior Art It was analyzed how differences at nano level between the Au-adsorbed $SnO_2$s of the disclosure and the prior led to significant differences in gas sensing applications capable of actually measuring surface/interface responses.

In relation to surface/interface reactions using $NO_2$-based gas sensing, the AU-embedded $SnO_2$ structure was much better than the bare $SnO_2$ and Au-adsorbed $SnO_2$ structures in such gas sensing indexes as response, response time, and recovery time. For example, as shown in FIG. 6, among bare $SnO_2$ of FIG. 6a, open-type $SnO_2$ of FIG. 6b having no thin film formed on the Au particles, and AU-embedded $SnO_2$ of FIG. 6c having a thin Sn-rich $SnO_2$ thin film formed on the Au particles by the FCVD, the AU-embedded $SnO_2$ exhibited highest sensitivity and gas adsorption/desorption efficiency at each $NO_2$ concentration (e.g., 2, 6, and 10 ppm) (FIG. 6g for response, FIG. 6h for response time, and FIG. 6i for recovery time). As shown in Table 1 below, response to $NO_2$ gas were higher while response time and recovery time were shorter.

TABLE 1

Gas sensing indexes (e.g., response, response time, and recovery time) of bare $SnO_2$, Au-adsorbed $SnO_2$, and Au-embedded $SnO_2$

|  | bare $SnO_2$ | | | Au-adsorbed $SnO_2$ | | | Au-embedded $SnO_2$ | | |
| --- | --- | --- | --- | --- | --- | --- | --- | --- | --- |
|  | 2 ppm | 6 ppm | 10 ppm | 2 ppm | 6 ppm | 10 ppm | 2 ppm | 6 ppm | 10 ppm |
| Response (Rg/Ra) | 17.08 | 25.8 | 29.53 | 17.45 | 27.78 | 31.97 | 23.3 | 37.87 | 41.68 |
| Response time (s) | 116 | 130 | 225 | 104 | 67 | 46 | 75 | 264 | 231 |
| Recovery time (s) | 408 | 194 | 122 | 198 | 129 | 99 | 213 | 96 | 60 |

Such differences come from differences in mechanism between the two kinds samples, i.e., Au-adsorbed $SnO_2$ and AU-embedded $SnO_{2-x}$ and it may logically be explained that different carrier conduction channels are inevitable as described below.

The surface/interface responses to $NO_2$ gas in Au-adsorbed $SnO_2$ prepared by the conventional method sequentially proceed as follows: (1) $NO_2$ as an oxidizing gas takes electrons from oxygen in the air at a process temperature of 200° C. (2) The surface of Au-adsorbed SnO surrounded by oxygen loses electrons to oxygen. In this case, the Au catalyst plays a role as a spillover to prolong the response between $NO_2$ and $O_2$ and the sample. (3) In this case, the surface of Au-adsorbed $SnO_2$ replenishes the lost electrons from the electron conductance channeling inside $SnO_{2-x}$ (4) As a result, the width of the internal conduction channeling, which is deprived of electrons by the surface of the sample, decreases and, due to insufficient carriers, the overall resistance of Au-adsorbed $SnO_2$ increases. (5) While the reactive gas, $NO_2$, is continuously supplied, this chain reaction continues.

On the other hand, a buried catalyst synthesized by the FCVD has more complicated electron conduction channeling in $NO_2$ gas adsorption, different from that of the open-type catalyst. This is due to the effects of the Sn-rich $SnO_2$ thin film covering the Au particles. At the quantum level below 10 nanometers, the energy of the material is drastically varied even with a slight change in size. For CdS and CdSe, the relationship between nano-sized material and energy may be represented as follows:

[Equation 1]

$$\Delta E \cong \frac{\eta^2 \pi^2}{2R^2}\left[\frac{1}{m_e^*} + \frac{1}{m_h^*}\right] - \frac{1.8^2}{\varepsilon R} \quad (1)$$

where $\Delta E$ denotes the bandgap, $\eta$ denotes the Dirac constant, R denotes the nanoscale radius, $m_e^*$ and $m_h^*$ denote the electron effective mass and the hole effective mass, respectively, e denotes the elementary charge, and c denotes the bulk optical dielectric constant.

This means that the bandgap energy of the sample according to the nanoparticle size meets the following relationship: $\Delta E \propto 1/R^2 - 1/R$. Then, the energy of a two-dimensional nano thin film, e.g., the Sn-rich $SnO_2$ thin film surrounding the Au particles, may be explained as follows. An increase in two-dimensional surface energy may be directly related to an increase in surface tension from the outermost part. An increase in the surface energy when the Sn-rich $SnO_2$ thin film covers the Au particles over conventional Au-adsorbed $SnO_2$ may be explained as follows. When Au is simply adsorbed to $SnO_{2-x}$ an energy equilibrium is established at each characteristic surface (interface) as illustrated in FIG. 7a, as in the Youngs equation. In other words, the interfacial energy $\gamma(SnO_2\text{-air})$ between $SnO_2$ and air is the sum of the interfacial energy between $SnO_2$ and Au and the interfacial energy between Au and air, which form a θ-degree angle. In other words, the sum of the three different vectors is zero. However, if an Sn-rich $SnO_2$ thin film is formed on the Au nanoparticles as illustrated in FIG. 7b, the $SnO_2$-air interfacial energy is changed into the sum of the interfacial energy between $SnO_2$ and Sn-rich $SnO_2$ and the interfacial energy between Sn-rich $SnO_2$ and air, which form a θ-degree angle. In this case, since the curvature of Sn-rich $SnO_2$ surrounding Au is the same as the curvature of Au, the angle remains θ for the outermost surface material while only the size of the vector is changed. As a prominent feature exhibited in this case, as shown in FIG. 7c, as the thickness of the Sn-rich $SnO_2$ thin film decreases (i.e., as the size of the vector converges to 0), the contribution of the $SnO_2$—Sn-rich $SnO_2$ interfacial energy gradually decreases and, as the contribution converges to 0, the Sn-rich $SnO_2$-air interfacial energy, which is angled therefrom at θ degrees, may be maximized. Thus, the $SnO_2$-air interfacial energy may be close to the Sn-rich $SnO_2$-air interfacial energy. In contrast to conventional nanosize-related research which mostly focuses on low-dimensional nano sizes (zero-, or one-dimensional), this concept regards higher-dimensional nano sizes, e.g., two-, or three-dimensional, and may be used to make more contributions to raise the effects of nano sizes.

Such high Sn-rich $SnO_2$ surface energy may lower the activation energy for starting $NO_2$ gas sensing. Described below is a logic behind lowering the barrier energy for triggering $NO_2$ to react to the surface. This starts from a change in free energy including surface energy represented as $dG = -sdT + vdP + \gamma dA$ (where dG, s, dT, v, dP, γ, and dA denote the changes in Gibbs free energy, entropy, temperature, volume, pressure, surface energy, and cross-sectional area, respectively. Under a certain temperature and pressure, the dT and dP terms become 0, i.e., $dG/dA = \gamma$. Thus, the surface energy increases as the cross-sectional area decreases for the same dG. This means that the surface energy gradually increases as the thickness of the Sn-rich $SnO_2$ thin film surrounding the semi-spherical Au catalyst as illustrated in FIG. 8a decreases as illustrated in FIGS. 8b and c. This may be shown in plan view as illustrated in FIG. 8d and in side view as illustrated in FIG. 7c. However, such an increase in the surface free energy of the AU-embedded $SnO_2$ sample prepared by the FCVD is not affected only by the cross-sectional area of Sn-rich $SnO_2$. It may be identified from FIG. 9 that the Gibbs free energy of Sn (FIG. 9a) is higher than the Gibbs free energy of $SnO_2$ (FIG. 9b) in all the temperature ranges. By the processing characteristics of the FCVD, if $SnO_2$ is changed into Sn-rich $SnO_2$, the Gibbs free energy is increased due to the difference in composition. In other words, from the above formula, the Sn-rich $SnO_2$ thin film formed on the Au particle serves to increase surface energy as compared with $SnO_2$.

This may be better understood from FIG. 10 which illustrates the relationship between Gibbs free energy and reaction process in different situations. FIG. 10 shows different changes in energy when $SnO_2 + NO_2$ is formed using different $SnO_2$ reactants in the same process. FIG. 10a shows changes in energy while $NO_2$ gas is adsorbed to bare $SnO_2$, as the reactant, forming $SnO_2 + NO_2$. If an Au catalyst is added to bare $SnO_2$ as shown in FIG. 10b, the reaction may be accelerated by the known role of the Au catalyst which lowers activation energy Ea. Referring to FIG. 10c, since the $SnO_2$ thin film has much higher surface energy than $SnO_2$, and high surface energy due to a change in composition (from $SnO_2$ to Sn-rich $SnO_2$) is added, the initial Gibbs free energy of $SnO_2$ is increased, rather than the activation energy being lowered, in the path from the $SnO_2$ reactant to the product of $SnO_2 + NO_2$. Resultantly, the activation energy is lowered in the entire reaction, so that the reaction from the reactant to the product may quicken. Thus, as illustrated in FIG. 10d, it is possible to obtain both the advantages shown in FIG. 10b and the advantages shown in FIG. 10c by forming an Sn-rich $SnO_2$—Au—$SnO_2$ structure by the FCVD. A multi-layered, quantum-sized thin Sn-rich $SnO_2$ film may be formed by adjusting the processing time of FCVD and, in such a case, changes in size and composition may drastically increase surface energy. The thickness of the Sn-rich $SnO_2$ thin film is within the Debye length range of $SnO_{2-x}$ so that gas sensing is prominent. Therefore, Au may fall within the Debye length range, meaning that although the although surrounded by the Sn-rich $SnO_2$ film, Au particles may sufficiently serve as a spillover. Therefore, the unique structure of Au-embedded $SnO_s$ synthesized by the FCVD, which takes both the effects (surface energy increase and Catalyst effect) is inevitably advantageous for gas sensing.

A buried gas sensing mechanism is described below stepwise from the adsorption of reactive gas to the final change in resistance. (1) $NO_2$ as reactive gas takes electrons from oxygen in the air at a process temperature. (2) Oxygen surrounding the sample takes electrons from the surface of the sample. Since an Sn-rich $SnO_2$ thin film is formed at the surface of the sample formed by the FCVD, the surface energy is sharply increased by the nanosize effect and the change in composition from $SnO_2$ to Sn-rich $SnO_{2-x}$ so that an electron conduction layer is directly formed on the surface. (3) Further, since the Sn-rich $SnO_2$ film is very thin (even smaller than the Debye length), the Au particles inside the Sn-rich $SnO_2$ film may also promote the spillover for $NO_2$ gas. (4) In this case, the reaction proceeds on the entire surface of AU-embedded $SnO_{2-x}$ so that there is no need for taking electrons from the electron conduction channeling inside $SnO_2$ to replenish the lost electrons. (5) As a result, the width of the internal conduction channeling, which is deprived of electrons by the surface of the sample, decreases and, due to insufficient carriers, the overall resistance of Au-embedded $SnO_2$ increases. (6) While the reactive gas, $NO_2$, is continuously supplied, this chain reaction continues.

As described above, while the conventional method enhances gas sensing reaction by prolonging the gas reaction time by the spillover of Au, the FCVD forms a metallic surface and raises surface energy by a nano thin film and changes in composition, thereby directly enhancing gas sensing reaction while taking the advantageous of Au spillover. Thus, the Sn-rich $SnO_2$—Au—$SnO_2$ sample prepared by the FCVD exhibited much higher superiority in response, response time, and recovery time. Nanosize effects and composition change effects are given to the surface, so that the energy distribution of the sample is rearranged, thereby lowering the activation energy necessary for reaction while maintaining the advantages of the catalyst, and increasing the sensitivity and speed of the gas sensing reaction at the surface/interface. It takes five seconds to apply such nano-size effects and composition change effects.

As compared with the conventional Au-adsorbed $SnO_2$ sample in which no thin film is formed on the Au particles, forming a nano-sized thin film on the Au particles, like in a sample prepared by the FCVD, may significantly change the physicochemical properties. This is meaningful as the first attempt to lead a new two-dimensional change from nano-size, the first stage. The FCVD and the AU-embedded $SnO_2$ nanocomposite may have applications in various sectors.

What is claimed is:

1. A gold (Au)-embedded triple-layer $SnO_2$ nanocomposite, comprising three layers of $SnO_2$—Au—$SnO_2$-x (0<x<2), wherein the Au is buried between the $SnO_2$ and $SnO_{2-x}$ (0<x<2) layers.

2. The Au-embedded triple-layer $SnO_2$ nanocomposite of claim 1, wherein a $SnO_2$-x (0<x<2) nano-thin film is formed on Au nanoparticles.

3. The Au-embedded triple-layer $SnO_2$ nanocomposite of claim 2, wherein the $SnO_{2-x}$ (0≤x<2) nano-thin film has a thickness of 3 nm to 5 nm.

4. A method for manufacturing an Au-embedded triple-layer $SnO_2$ nanocomposite, the method comprising:
   putting organic materials containing Au and a metal salt on an $SnO_2$ nanowire; and
   adsorbing the Au on the $SnO_2$ nanowire by instantly vaporizing the organic materials, except for the Au, by flame chemical vapor deposition (FCVD), wherein the Au-embedded triple-layer $SnO_2$ nanocomposite comprises three layers of $SnO_2$—Au—$SnO_2$-x (0≤x<2), and wherein Au is buried between the $SnO_2$ and $SnO_{2-x}$ (0≤x<2) layers.

5. The method of claim 4, wherein an $SnO_2$-x (0≤x<2) nano-thin film is formed on Au nanoparticles.

6. The method of claim 4, wherein the organic materials containing the Au and the metal salt are $HAuCl_4.4H_2O$ (l) and $(CH_3)_2CHOH$ (l), respectively.

7. The method of claim 4, wherein the FCVD includes directly radiating a flame at 1200° C. to 1500° C. for 3 seconds to 7 seconds.

8. A gas sensor, comprising: an Au-embedded triple-layer $SnO_2$ nanocomposite including three layers of $SnO_2$—Au—$SnO_2$-x (0≤x<2), wherein the Au is buried between the $SnO_2$ and $SnO_{2-x}$ (0≤x<2) layers.

9. The gas sensor of claim 8, wherein a $SnO_2$-x (0≤x<2) nano-thin film is formed on Au nanoparticles.

10. The gas sensor of claim 8, wherein the $SnO_{2-x}$ (0≤x<2) nano-thin film has a thickness of is 3 nm to 5 nm.

11. The gas sensor of claim 8, further comprising:
   a substrate; and
   an electrode disposed on the substrate, wherein
   the Au-embedded triple-layer $SnO_2$ nanocomposite is formed on an upper surface, a lower surface, or a side surface.

* * * * *